US008524882B2

(12) United States Patent
Gebeyehu et al.

(10) Patent No.: US 8,524,882 B2
(45) Date of Patent: *Sep. 3, 2013

(54) METHOD FOR DEBLOCKING OF LABELED OLIGONUCLEOTIDES

(75) Inventors: Gulilat Gebeyehu, Potomac, MD (US); Richard Pires, Mount Airy, MD (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,907

(22) Filed: Jun. 3, 2011

(65) Prior Publication Data

US 2012/0253028 A1    Oct. 4, 2012

Related U.S. Application Data

(63) Continuation of application No. 10/365,644, filed on Feb. 13, 2003, now Pat. No. 8,093,372, which is a continuation of application No. 09/576,555, filed on May 24, 2000, now Pat. No. 6,593,464.

(60) Provisional application No. 60/135,848, filed on May 24, 1999.

(51) Int. Cl.
*C07H 21/00* (2006.01)

(52) U.S. Cl.
USPC ..................................... 536/25.31

(58) Field of Classification Search
None
See application file for complete search history.

(56) References Cited

U.S. PATENT DOCUMENTS

| | | | |
|---|---|---|---|
| 4,055,469 A | 10/1977 | Snoke et al. | |
| 4,415,732 A * | 11/1983 | Caruthers et al. | 536/26.5 |
| 4,419,509 A | 12/1983 | Hsiung | |
| 4,458,066 A | 7/1984 | Caruthers et al. | |
| 4,739,044 A | 4/1988 | Stabinsky | |
| 4,757,141 A | 7/1988 | Fung et al. | |
| 4,797,480 A | 1/1989 | Sorbi et al. | |
| 4,965,349 A * | 10/1990 | Woo et al. | 536/25.3 |
| 4,997,928 A | 3/1991 | Hobbs | |
| 5,262,536 A | 11/1993 | Hobbs, Jr. | |
| 5,428,148 A | 6/1995 | Reddy et al. | |
| 5,472,672 A | 12/1995 | Brennan | |
| 5,514,789 A | 5/1996 | Kempe | |
| 5,518,651 A | 5/1996 | Reddy et al. | |
| 5,529,756 A | 6/1996 | Brennan | |
| 5,539,097 A | 7/1996 | Arnold, Jr. | |
| 5,623,068 A * | 4/1997 | Reddy et al. | 536/25.34 |
| 5,736,626 A | 4/1998 | Mullah et al. | |
| 5,738,829 A | 4/1998 | Kempe | |
| 5,756,705 A * | 5/1998 | Wang | 536/25.32 |
| 5,756,838 A | 5/1998 | Davis et al. | |
| 5,773,590 A | 6/1998 | Hart et al. | |
| 5,804,375 A | 9/1998 | Gelfand | |
| 5,888,397 A | 3/1999 | Rogers et al. | |
| 5,897,838 A * | 4/1999 | Kempe | 422/530 |
| 5,942,609 A * | 8/1999 | Hunkapiller et al. | 536/25.3 |
| 6,090,934 A | 7/2000 | Kumar et al. | |
| 6,255,476 B1 | 7/2001 | Vinayak et al. | |
| 6,296,787 B1 * | 10/2001 | Akhavan-Tafti et al. | 252/700 |
| 6,468,743 B1 * | 10/2002 | Romick et al. | 435/6.12 |
| 6,583,168 B1 * | 6/2003 | Menchen et al. | 514/410 |
| 6,593,464 B1 * | 7/2003 | Gebeyehu et al. | 536/25.31 |
| 6,664,388 B2 * | 12/2003 | Nelson | 536/25.31 |
| 8,093,372 B2 * | 1/2012 | Gebeyehu et al. | 536/25.31 |
| 2002/0090635 A1 | 7/2002 | Xia et al. | |
| 2002/0143166 A1 | 10/2002 | Pires et al. | |

FOREIGN PATENT DOCUMENTS

| | | |
|---|---|---|
| EP | 0063879 | 3/1982 |
| EP | 0323152 | 7/1989 |
| EP | 0786468 | 7/1997 |
| GB | 2125789 | 3/1984 |
| JP | 200796 | 1/1990 |
| JP | 07505904 | 6/1995 |
| JP | 090504950 | 5/1997 |
| JP | 09208595 | 8/1997 |
| WO | WO93/22329 | 11/1993 |
| WO | WO95/13399 | 5/1995 |
| WO | WO98/23774 | 6/1998 |
| WO | WO99/38962 | 8/1999 |
| WO | WO00/71559 | 11/2000 |

OTHER PUBLICATIONS

Boal et al., "Cleavage of Oligodeoxyribonucltides from Controlled-pore Glas Supports and Their Rapid Deprotection by Gaseous Amines," Nucleic Acids Research, 24(15), 3115-3117 (Aug. 1996).*
Mullah et al., "Efficient Synthesis of Double Dye-Labeled Oligodeoxy-ribonucleotide Probes and Their Application in a Real Time PCR Assay," Nucleic Acids Research, 26(4), 1026-1031 (Feb. 15, 1998).*
Costa et al., "Cloning and Analysis of PCR-generated DNA Fragments", *in peR Primer: A Laboratory Manual, Dieffenbach, C.W. and Dveksler,G.S., eds*.,, Cold Spring Harbor Laboratory Press, Cold Spring Harbor, NY,, 1995, 555-580.
Crea et al., "Synthesis of oligonucleotides on cellulose by a phosphotriester method", *Nucleic Acids Research*, vol. 8, No. 10, May 24, 1990, 2331-2348.
EP Application No. 00937721.9, European Search Report, mailed Jun. 3, 2002.
Gait et al., "Chapter 2: Oligoribonucleotide synthesis", *in: Oligonucleotides and Analogues: A Practical Approach, Eckstein, F. r ed*., IRL Press at Oxford University Press, Oxford, Great Britain, 1991, 25-48.
Gough et al., "2' (3')-O-Benzoyluridine 5' Linked to Glass: An All-Purpose Support for Solid Phase Synthesis of Oligodeoxyribonucleotides", *Tetrahedron Letters*, vol. 24, No. 48, 1983, 5321-5324.
Jinks et al., "Molecular genetic diagnosis of sickle cell disease using dried blood specimens on blotters used for newborn screening", *Human Genetics*, vol. 81, No. 4, Mar. 1989, 363-366.

(Continued)

*Primary Examiner* — Lawrence E Crane

(57) ABSTRACT

The invention relates to a process for deblocking substantially a blocked, detectably labeled oligonucleotide by contacting the blocked detectably labeled oligonucleotide with an effective amount of a nucleophilic amino compound under conditions that result in substantial deblocking of the oligonucleotide, thereby giving the substantially deblocked oligonucleotide.

20 Claims, 6 Drawing Sheets

(56) References Cited

OTHER PUBLICATIONS

JP Application No. 2000-619814, Office Action mailed Oct. 4, 2010.
JP Application No. 2000-619814, Response to Oct. 4, 2010 Office Action filed Mar. 30, 2011.
Life Technologies, "DNA Isolation", *Gibco BRL*, in: Product Catalogue and Reference Guide. Life Technologies. Gaithersburg. MD., 1995, 14-2 to 14-18 and 18-36 to 18-37.
Lyttle et al., "A new universal linker for solid phase DNA synthesis", *Nucleic Acids Research*, vol. 24, No. 14, Jul. 15, 1996, 2793-2798.
Lyttle et al., "A Phosphate Bound Universal Linker for DNA Synthesis", *Nucleosides & Nucleotides*, vol. 18, No. 8, Aug. 1999, 1809-1824.
Lyttle et al., "Versatile Linker Chemistry for Synthesis of 3'-Modified DNA", *Bioconjugate Chemistry*, vol. 8, No. 2, Mar.-Apr. 1997, 193-198.
Matteucci et al., "Synthesis of Deoxyoligonucleotides on a Polymer Support", *Journal of the American Chemical Society*, vol. 103, No. 11, 1981, 3185-3191.
Nelson et al., "Rainbow Universal CPG: A Versatile Solid Support for Oligonucleotide Synthesis",*BioTechniques*, vol. 22, No. 4, Apr. 1997, 752-756.
International Application No. PCT/US2000/014274, International Search Report, mailed Aug. 31, 2000.
Reddy et al., "Fast Cleavage and Deprotection of Oligonucleotides", *Tetrahedron Letters*, vol. 35, No. 25, Jun. 20, 1994, 4311-4314.
Ruth, "Chapter 11:0ligodeoxynucleotides with reporter groups attached to the base", *in: Oligonucleotides and Analogues: A Practical Approach, Eckstein, F. , ed. ,,* IRL Press at Oxford University Press, Oxford, Great Britain,, 1991, 255-282.
Sinha et al., "Oligonucleotides with reporter groups atached to the 5'-terminus", *In Oligonucleotides and Analogues A Practical Approach, Eckestein, F. ed.,,* IRL Press, 1991, 185-210.
Tyagi et al., "Molecular Beacons: Probes that Fluoresce upon Hybridization", *Nature Biotechnology*, vol. 14, No. 3, Mar. 1996, 303-308.
Unknown, *Ac-dC, Glen Research, Online Product Information, Glen Research*, available at www.glenres.com, May 20, 1999, 6 pages.
Unknown, "Alternatives to Expedite Monomers", *Glen Research, Online Product Information*, May 20, 1999, 8.
Unknown, "Solid phase phosporamidite oligonucleotide synthesis", *in Oligonucleotides and Analogues. A Practical Approach, Eckstein, F. , ed. ,,* IRL Press, New York 1991, 2.2:4-9.
U.S. Appl. No. 09/245,023, filed Feb. 5, 1999 (Abandoned).
Waggoner, "Ch. 1: Fluorescent Probes for Analysis of Cell Structure, Function, and Health by Flow and Image Cytometry," in Applications of Fluorescence in the Biomedical Science, Taylor et al., ed. r Alan R. Liss, 1986, 3-28.

\* cited by examiner

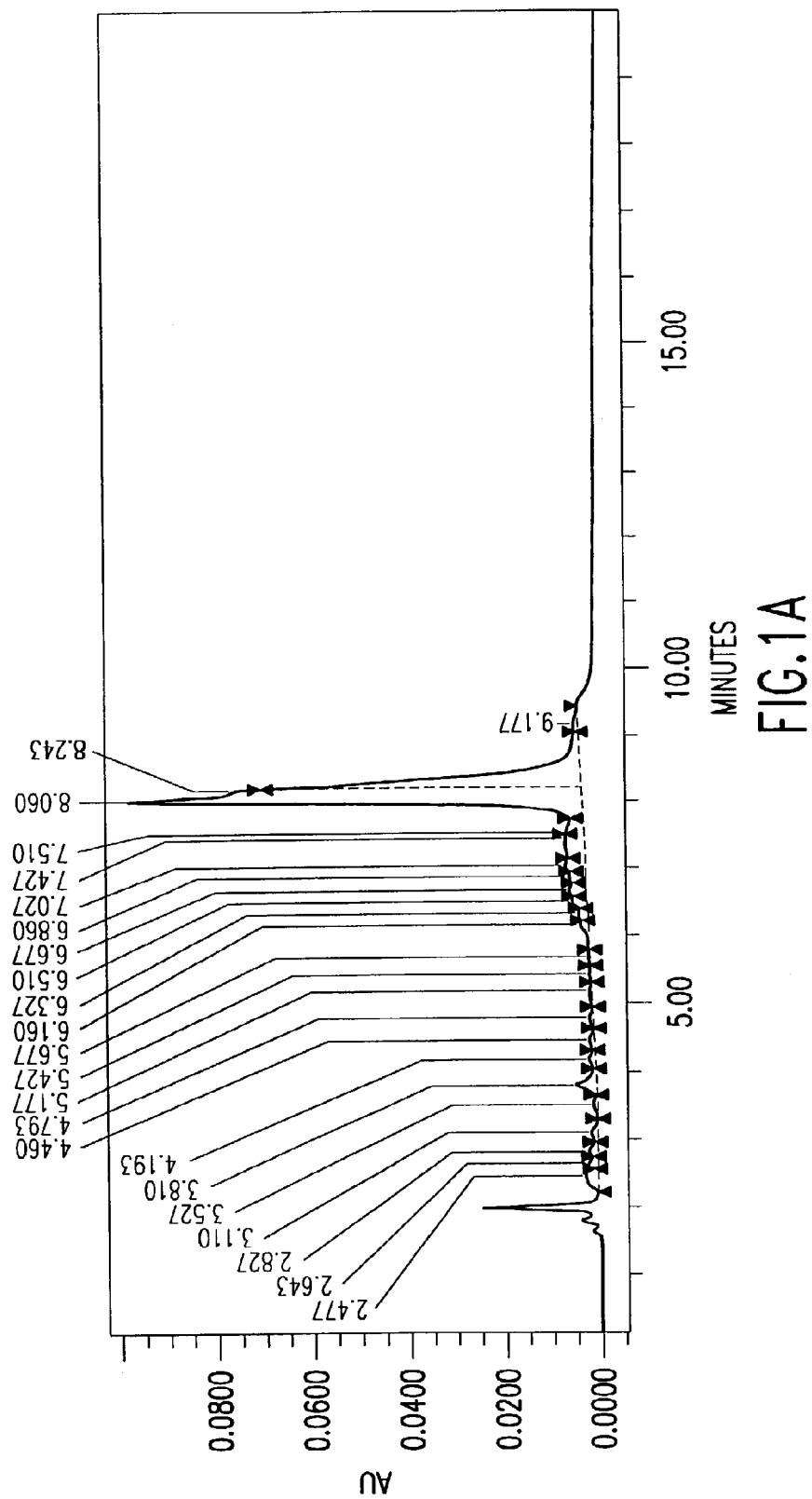

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial
<220> FEATURE:
<223> OTHER INFORMATION: Oligonucleotide

<400> SEQUENCE: 1
ggtccgacca gatggcgaaa ggcaaacgga                                    30

<210> SEQ ID NO 2
<211> LENGTH: 35
<212> TYPE: DNA
<213> ORGANISM: Artificial
<220> FEATURE:
<223> OTHER INFORMATION: Oligonucleotide

<400> SEQUENCE: 2
gcgacgcctg tcctccaatt tgtcctggtc gtcgc                              35
```

METHOD FOR DEBLOCKING OF LABELED OLIGONUCLEOTIDES

CROSS-REFERENCE TO RELATED APPLICATIONS

This application is a continuation of U.S. application Ser. No. 10/365,644 filed Feb. 13, 2003, now U.S. Pat. No. 8,093,372 which is a continuation of U.S. application Ser. No. 09/576,555 filed May 24, 2000, now U.S. Pat. No. 6,593,464 which claims priority to U.S. Application No. 60/135,848 filed May 24, 1999, which disclosures are herein incorporated by reference in their entirety.

BACKGROUND OF THE INVENTION

1. Field of the Invention

The present invention relates to processes for the substantial deprotection or deblocking of labeled oligonucleotides by use of an amino reagent such as ammonia.

2. Related Art

A variety of solid phase oligonucleotide synthesis techniques are known to those skilled in the art. Such techniques include phosphoramidite, phosphotriester, phosphodiester, phosphite and H-phosphonate methods and the like, each of which is generally known in the field of molecular biology. For example, the b-cyanoethyl phosphoramidite method is described in U.S. Pat. No. 4,458,066 issued to Caruthers, et al., entitled "Process for Preparing Polynucleotides," which is incorporated herein by reference.

The phosphoramidite based synthesis of oligonucleotides requires the protection of the exocyclic amino groups. The most commonly used protecting groups for this purpose are benzoyl for the 6-amino of adenine and 4-amino of cytosine and isobutyroyl for 2-amino of guanine. Oligonucleotides are synthesized on solid support using nucleoside phosphoramidites where the amino groups are protected as shown below.

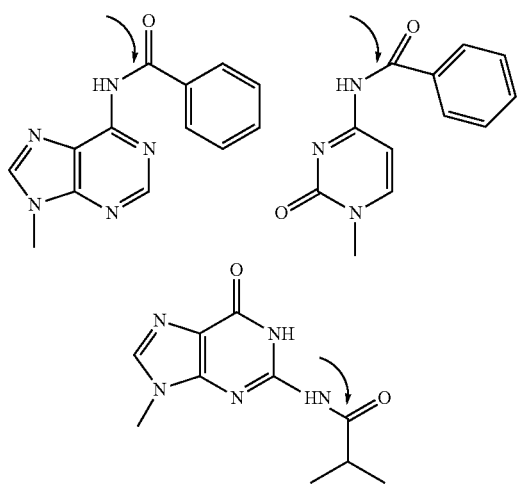

After the synthesis is completed the oligonucleotide is cleaved from the support and these protecting groups are removed by hydrolysis at high temperatures using concentrated ammonium hydroxide. After hydrolysis, the ammonium hydroxide has to be evaporated in order to obtain the desired oligonucleotide.

The use of hot concentrated ammonium hydroxide for the removal of these protecting groups has restricted the modified bases that can be used to those that can withstand these harsh conditions. For modified oligos such as dye containing oligos, heating in ammonium hydroxide can not be used since the dyes are not stable under these conditions. In general, dye labeled oligos are deprotected by treatment with ammonium hydroxide at room temperature for over 24 hours or require special reagents for this purpose. See U.S. Pat. No. 4,965,349. Alternatively, oligos may prepared using phosphoramidite having easily removable protecting groups which do not require the use of hot concentrated ammonium hydroxide. See Boal, J. H. et al., Nucl. Acids Res. 24:3115-3117 (1996).

The standard method where deprotection with concentrated ammonium hydroxide is done at reduced temperature results in incomplete deprotection and over all low quality of dye labeled oligonucleotides. Often this requires tedious purification which results in low yield.

U.S. Pat. No. 4,965,349 describes a method of hydrolyzing base-labile linking groups between a solid phase support and oligonucleotides with a reagent comprising a lower alcohol, water and a non-nucleophilic hindered alkylamine. According to this patent, this cleavage reagent preserves the fluorescent characteristics of rhodamine dyes during cleavage from the solid support.

U.S. Pat. No. 5,514,789 describes a method for the cleavage and deprotection of newly synthesized oligonucleotides from solid supports with a gaseous cleavage/deprotection reagent such as gaseous ammonia, ammonium hydroxide vapors, and methylamine.

U.S. Pat. No. 5,518,651 describes a method for the cleavage and deprotection of insolubilized and protected oligonucleotides using an alkyl amine, e.g. t-butylamine and methylamine. According to this patent, the deprotection and cleavage of the oligonucleotides occurs at room temperature and in less than about 90 min.

U.S. Pat. No. 5,738,829 describes a method for the cleavage and deprotection of oligonucleotides from solid supports which involves incubation of the immobilized oligonucleotides with gaseous ammonia or ammonium hydroxide vapors. According to this patent, the method lends itself to the use of supports such as microtiter plates that can be used to perform up to 96 individual synthetic processes.

Glenn Research of Sterling Va. offers phenoxyacetyl protected dA, 4-isopropylphenoxylacetyl protected dG and acetyl protected dC which can be used to prepare oligonucleotides. According to Glenn Research's web site, these monomers can be used with sensitive labeling reagents such as TAMRA, Cy5® and HEX since cleavage and deprotection can be carried out in 2 hours at room temperature with ammonium hydroxide or 0.005 M potassium carbonate in anhydrous methanol. In addition, according to this web site, it is possible to deprotect oligonucleotides containing acetyl protected dC monomers by treatment with ammonium hydroxide/methylamine for 10 min at 65° C. or less.

We have now found that the use of nucleophilic amino compounds under pressure and high temperature is an effective way to deprotect dye labeled oligos. The dye labeled oligos deprotected in this manner are fully deprotected and are of high quality. In addition, the process is simple and saves time, reducing the deblocking (processing) time from approximately 28 hours to 1 hour.

BRIEF SUMMARY OF THE INVENTION

The invention relates to a process for deblocking a detectably labeled oligonucleotide comprising contacting the blocked detectably labeled oligonucleotide with an effective amount of a nucleophilic amino compound under conditions that result in the deblocking of the oligonucleotide, thereby giving the deblocked oligonucleotide.

BRIEF DESCRIPTION OF THE DRAWINGS

FIGS. 1A and 1B depict ion-pair HPLC chromatograms showing the analysis of the dye labeled oligo (5'-FAM-GGT CCG ACC AGA TGG CGA AAG GCA AAC GGA; SEQ ID NO:1) after deprotection with concentrated ammonium hydroxide, RT, 24 hrs (FIG. 1A) or with gaseous ammonia (80 psi), 95° C., 45 min (FIG. 1B). Buffer A=5 mM TBAP in 20 mM $NH_4HPO_4$. Buffer B=$CH_3CN$, gradient of 40% B to 60% B over 10 min, flow rate of 2 ml/min.

DETAILED DESCRIPTION OF THE INVENTION

Figure 1B:
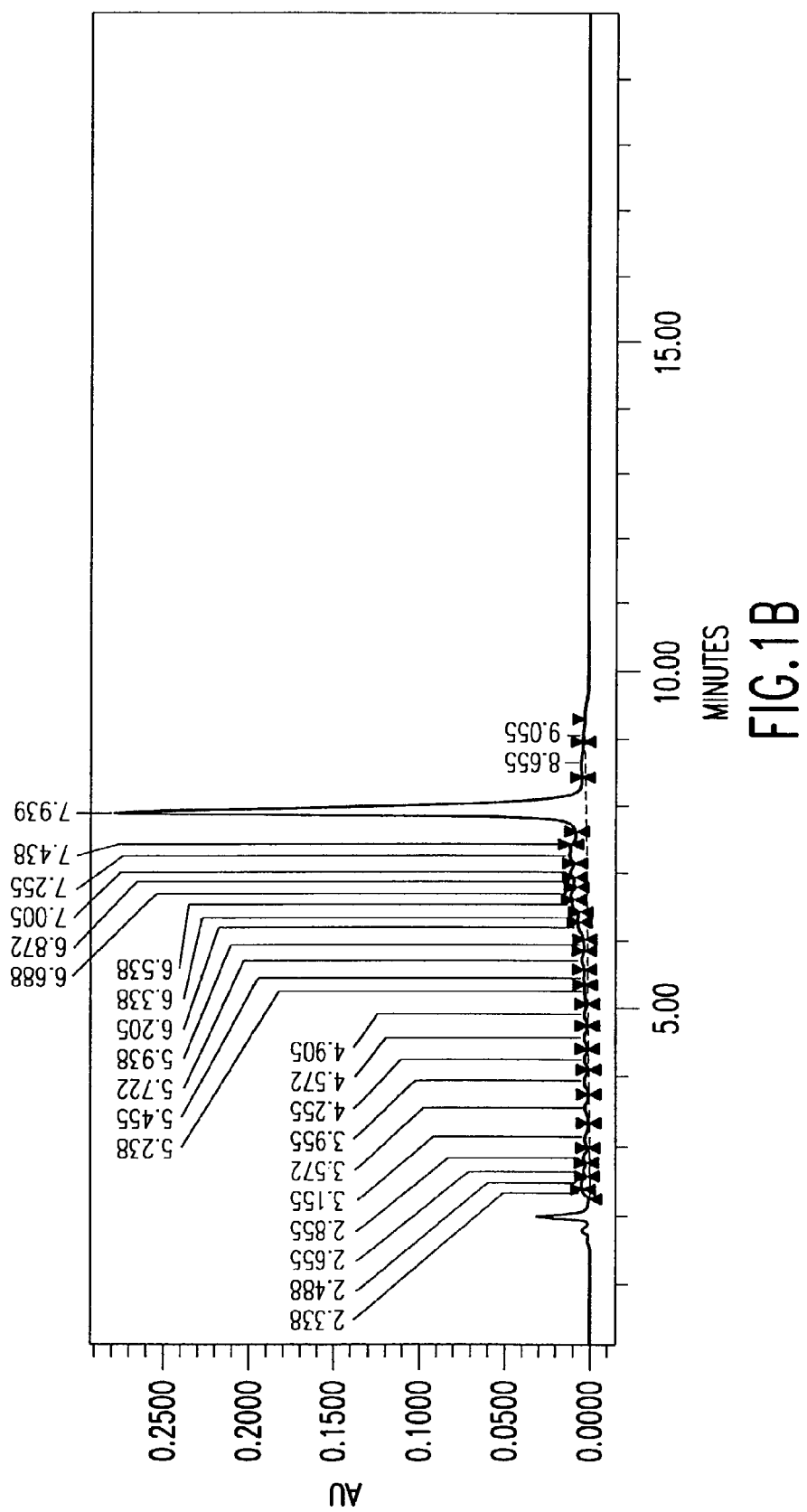
Figure 2A:
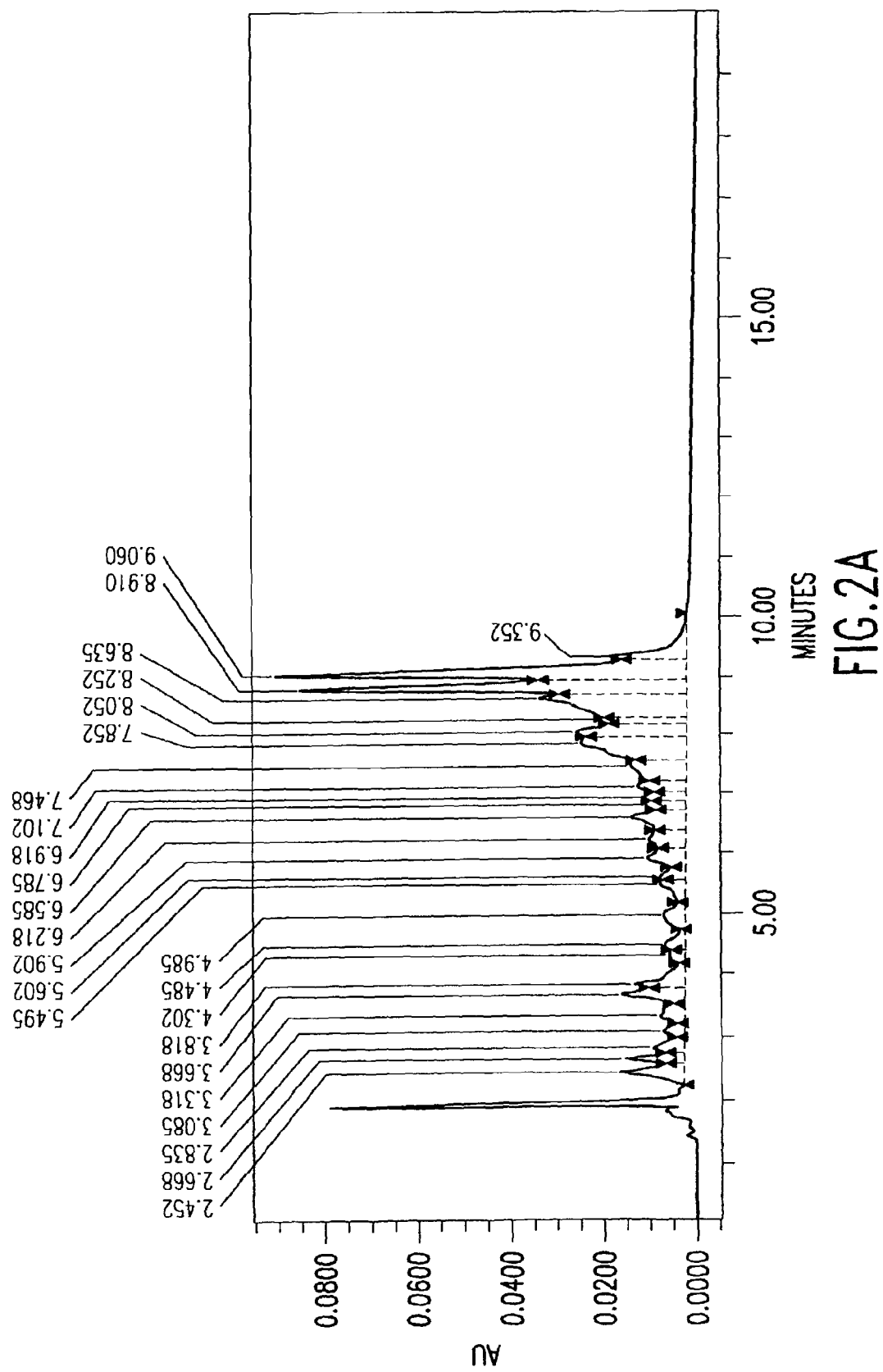
FIGS. 2A-2D depict ion-pair HPLC chromatograms showing the analysis of molecular beacon (5'-HEX-GCG ACG CCT GTC CTC CAA TTT GTC CTG GTC GTC GC DAB-CYL) after deprotection with concentrated ammonium hydroxide, 90° C., 75 min (FIG. 2A), concentrated ammonium hydroxide, RT, 24 hrs (FIG. 2B), concentrated ammonium hydroxide, RT, 40 hrs (FIG. 2C), or with gaseous ammonia (80 psi), 95° C., 1 hr (FIG. 2D). Buffer A=5 mM TBAP in 20 mM $NH_4HPO_4$. Buffer B=$CH_3CN$, gradient of 40% B to 60% B over 10 min, flow rate of 2 ml/min.
Figure 2B:
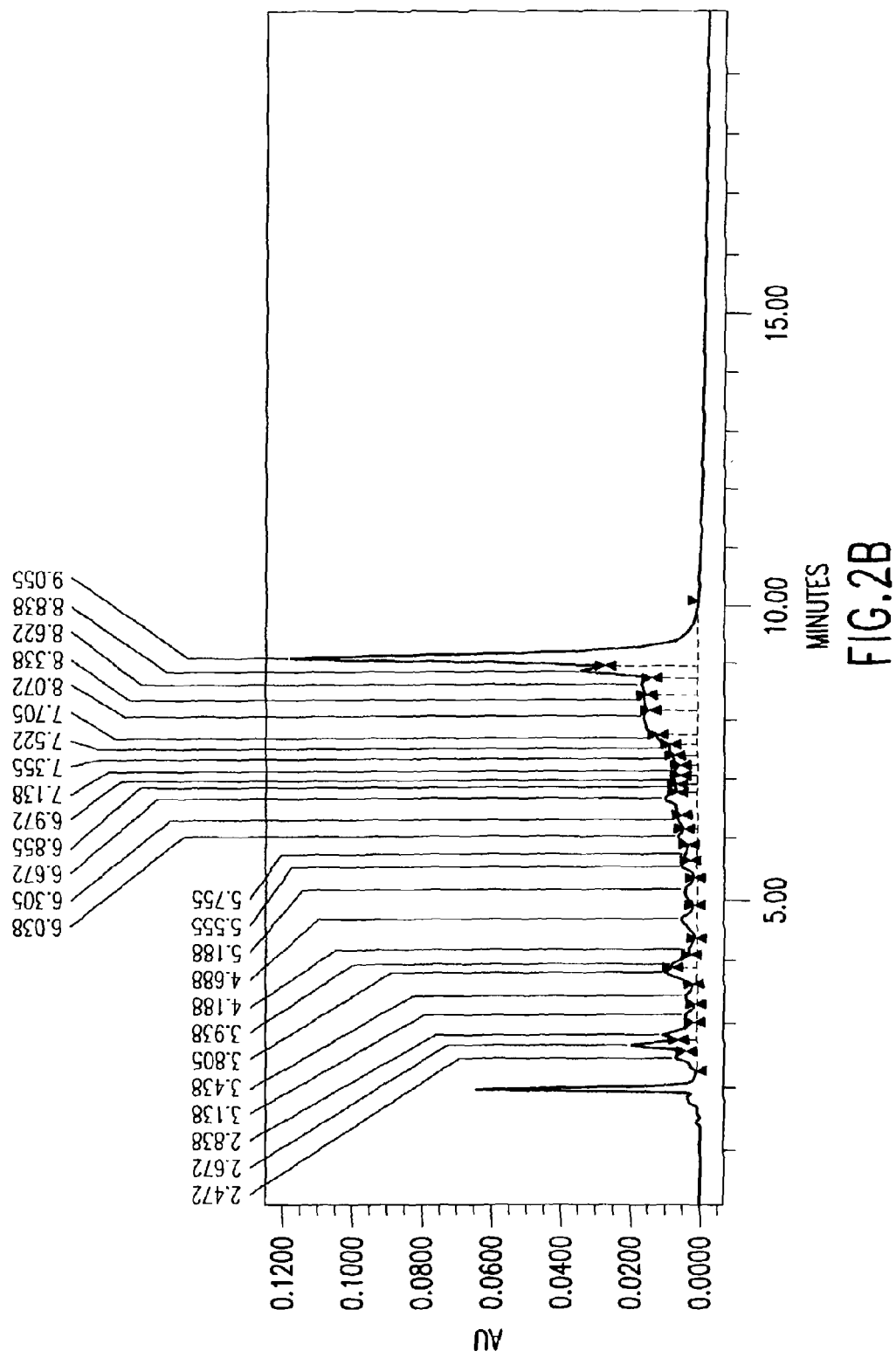
Figure 2C:
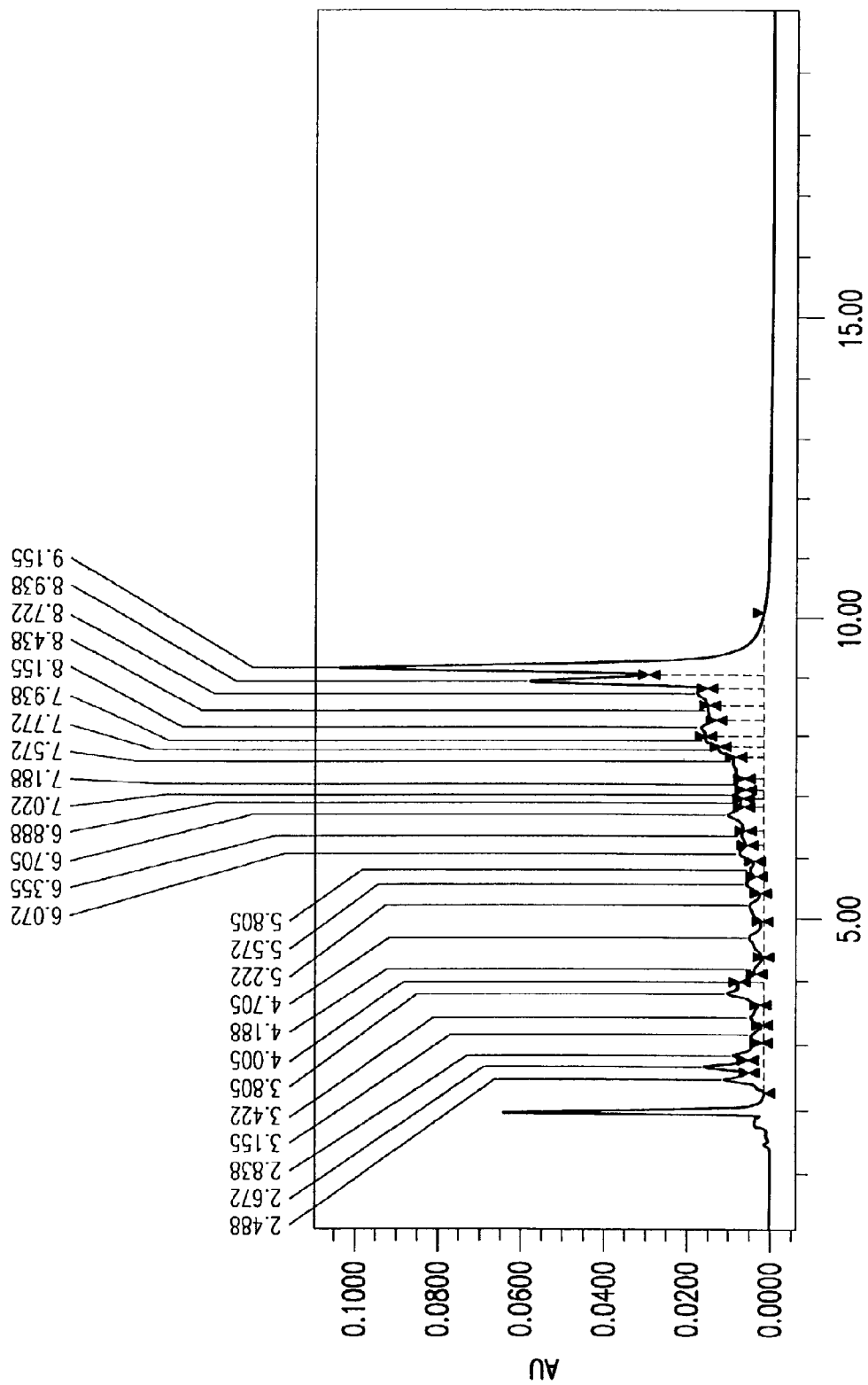
Figure 2D:
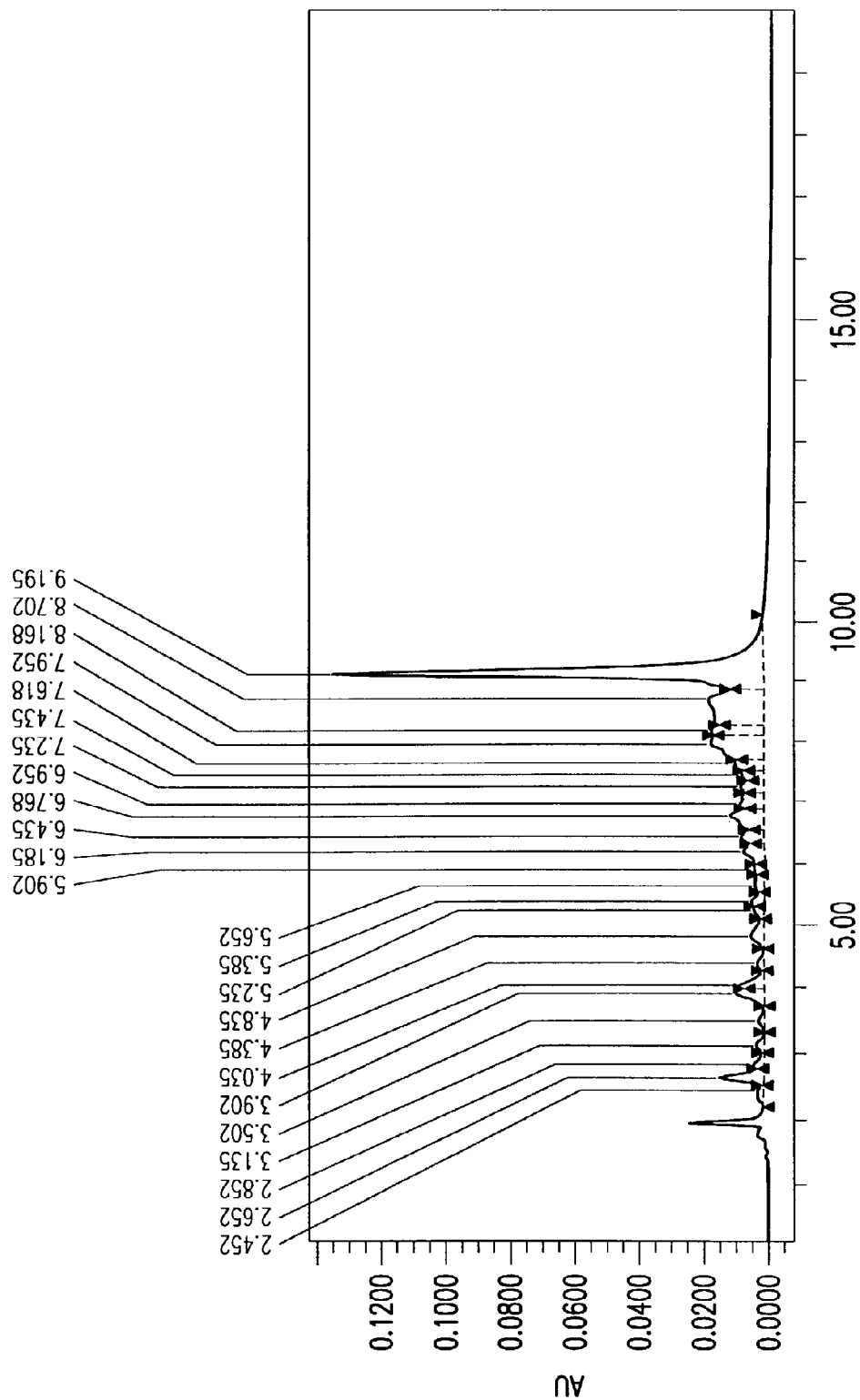

The invention relates to a process for deblocking substantially detectably labeled oligonucleotides comprising contacting the blocked detectably labeled oligonucleotide with an effective amount of a deblocking reagent such as a nucleophilic amino compound. Preferably, the deblocking reagent is gaseous at ambient temperature.

The present invention provides a number of advantages over conventional methods of deblocking oligonucleotides using aqueous ammonia, including improved quality (purity) of the deblocked oligonucleotide, higher yield, and shorter reaction times. Moreover, the amino compound may be removed substantially by degassing (in the case of ammonia, methylamine and ethylamine), thus providing ease of recovery of the deblocked oligonucleotide. In the case of higher molecular weight amino compounds that are liquids at room temperature, the amino compound may be removed by washing the deblocked oligonucleotide with an organic solvent in which the oligonucleotide is poorly soluble, e.g. acetonitrile, diethyl ether and the like, to remove the amino compound. The deblocked oligonucleotide may then be resuspended directly in water, a buffer or other solution and used directly as a molecular biology reagent, e.g. as a diagnostic reagent in sequencing, PCR or as a probe. The buffer may be chosen to neutralize any residual nucleophilic amino compound (e.g. ammonia) that may be present. Particularly preferred buffers are the acetate, sulfate, hydrochloride, phosphate or free acid forms of Tris-(hydroxymethyl)amino-methane (TRIS®), although alternative buffers of the same approximate ionic strength and pKa as TRIS® may be used with equivalent results. Other preferred buffers are triethyl ammonium salts (e.g. the acetate salt). In addition to the buffer salts, cofactor salts such as those of potassium (preferably potassium chloride or potassium acetate) and magnesium (preferably magnesium chloride or magnesium acetate) may be included. Addition of one or more carbohydrates and/or sugars to the buffer solution and/or deblocking reaction mixtures may also be advantageous, to support enhanced stability of the product upon storage. Preferred such carbohydrates or sugars include, but are not limited to, sucrose, trehalose, and the like. Such carbohydrates and/or sugars are commercially available from a number of sources, including Sigma (St. Louis, Mo.).

The nucleophilic amino compound may be ammonia or ammonia vapors (e.g. obtained by heating a sealable chamber having a quantity of ammonium hydroxide in the bottom), or a $C_{1-6}$ alkylamino compound. The alkyl group may be straight or branched chain. Examples of such alkylamino compounds include methylamine, ethylamine, propylamine, isopropylamine, butylamine, sec-butylamine, pentylamine and hexylamine. When the nucleophilic amino compound is a liquid at ambient temperature, it may be removed under vacuum with or without heating. In a preferred embodiment, the nucleophilic amino compound is at least saturated with water vapor.

The label on the oligonucleotide may be any conventional label used for detection of oligonucleotides, including, without limitation, fluorescent dyes chosen from the group consisting of xanthenes (e.g., fluoresceins, eosins, erythrosins), rhodamines (e.g., Texas Red®), benzimidazoles, ethidiums, propidiums, anthracyclines, mithramycins, acridines, actinomycins, merocyanines, coumarins (e.g., 4-methyl-7-methoxycoumarin), pyrenes, chrysenes, stilbenes, anthracenes, naphthalenes (e.g., dansyl, 5-dimethylamino-1-naphthalenesulfonyl), salicylic acids, benz-2-oxa-1-diazoles (also known as benzofurans) (e.g., 4-amino-7-nitrobenz-2-oxa-1,3-diazole), indodicarbocyanines (e.g. Cy3® and Cy5®, available from Biological Detection Systems, Inc.), fluorescamine, and psoralen. See U.S. Pat. Nos. 4,997,928, 5,262,536, and EP 63,879. Useful forms of many of these dyes are commercially available. See also A. W. Wagner, Chapter 1, Applications of Fluorescence in the Biomedical Sciences, Taylor et al. (ed.), Alan R. Liss, New York (1986). Particular examples include 6-(fluorescein-6-carboxamido)hexanoate (6-FAM), fluorescein isothiocyanate (FITC), hexachlorofluorescein (HEX), tetrachlorofluorescein (TET), 6-carboxy-4',5'-dichloro-2',7'-dimethoxyfluorescein (6-JOE), and BODIPY. In a preferred embodiment, the oligonucleotides is labeled with the molecular beacon technology according to Tyagi, S, and Kramer, F. R., *Nature Biotechnology* 14:303-308 (1996). One label that degrades in the presence of ammonia is (6-tetramethylrhodamine (TAMRA).

The blocked, labeled oligonucleotides may be prepared by well known methods, e.g. the phosphoramidite, phosphotriester, phosphodiester, phosphite and H-phosphonate methods, each of which are generally known in the field of molecular biology. For example, the b-cyanoethyl phosphoramidite method is described in U.S. Pat. No. 4,458,066 issued to Caruthers, et al., entitled "Process for Preparing Polynucleotides," which is incorporated herein by reference. See also E. Eckstein (ed.), Oligonucleotides and Analogs, A Practical Approach, IRL Press, Oxford (1991); GB 2,125,789; and U.S. Pat. Nos. 4,415,732, 4,739,044 and 4,757,141. Such oligonucleotides may be DNA, RNA, mixture of DNA and RNA, derivatives of DNA and RNA and mixtures thereof. In the case of RNA, base stable 2'-protecting groups are preferred. The blocked, labeled oligonucleotide may be free or immobilized on a solid phase which is also cleaved by the gaseous deblocking reagent. The deblocked oligonucleotide may then be recovered by washing the solid phase with water or a buffer.

The blocking group is present on the exocyclic amino groups of A, G and C. Thymine does not require protection. Such blocking groups may be $C_{1-6}$ alkanoyl (e.g. isobutyryl), aryloyl (benzoyl), phenoxyacetyl, $C_{1-6}$ alkoxyacetyl, and dimethyl formamidine (on $N^6$ of dA or $N^2$ of dG). When the deblocking reagent is an alkylamine, it is preferred that the base C be blocked with an acetyl group. The blocking group for the phosphorous may be a cyanoethyl group. All of these blocking groups are cleaved at the same time by the deblocking reagent.

The deblocking reaction is preferably carried out in a sealable chamber (although an open chamber may be used in accordance with the invention) that can be heated. Such sealable chambers include screw cap vials, Parr bottles, and the like. The oligonucleotide synthesis and cleavage from the support may be carried out with a commercially available DNA synthesizer, e.g. the ABI 380B DNA synthesizer, or other equipment that is set up for high throughput synthesis on a multi well channel, e.g. a 96 well plate (see, e.g., U.S. Pat. Nos. 5,472,672 and 5,529,756, and U.S. application Ser. No. 09/162,348, filed Sep. 28, 1998, which are incorporated herein by reference in their entireties).

The deblocking reagent is present in an amount effective to deblock the oligonucleotide. In general, the deblocking reagent is present in a large excess compared to the oligonucleotide. In the case of ammonia, the sealable chamber may be charged with about 20 to 200 psi of ammonia, most preferably, about 80 psi. Optimal amounts of the liquid alkylamino compounds may be determined with no more than routine experimentation.

The deblocking reaction is carried out at a temperature of about room temperature to about 150° C. Most preferably, when the deblocking reagent is ammonia, the reaction is carried out at about 95° C.

The deblocking reaction is carried out for about 1 min to about 2 hrs. More preferably, the reaction is carried out for about 1 min to about 1 hr. When the deblocking reagent is ammonia, it is preferred that the reaction be carried out for about 45 min.

By "substantially deblocked" is intended to mean that the blocked oligonucleotide is not detectable, e.g. by ion-pair HPLC, capillary electrophoresis or mass spectrometry, after the deblocking reaction according to the present invention.

The following examples are illustrative, but not limiting, of the method and compositions of the present invention. Other suitable modifications and adaptations of the variety of conditions and parameters normally encountered in molecular biology and chemistry, particularly oligonucleotide synthesis, which are obvious to those skilled in the art in view of the present disclosure are within the spirit and scope of the invention.

EXAMPLES

An example of deblocking of a fluorescein (FAM) labeled oligo under standard conditions (room temperature and 24 hrs) and also gas phase (45 min, 80 psi, 95° C.) is attached (FIGS. 1A and 1B). As can be seen from the chromatogram, the peak for the standard deblocking is broader indicating that there is an incomplete deprotection. However, the chromatogram deblocking with ammonia shows a much sharper peak which is indicative of complete deprotection and no degradation.

In another example an oligonucleotide labeled with hexachlorofluorescein (HEX) and DABCYL (molecular beacon) was deblocked under various conditions (FIGS. 2A-2D). Standard deblocking conditions (95° C., concentrated ammonia, 75 min, FIG. 2A) as well as room temperature treatment over 24 hours (FIG. 2B and FIG. 2C) show formation of a new peak which may be attributed to degradation of the dye. As can be seen from the chromatographs (FIG. 2D) deblocking under gas phase gives better quality oligonucleotides.

Experimental Procedure:

Place the dye-oligo-CPG (obtained from phosphoramidite based automated synthesis) in a high pressure reactor. Charge the reactor with gaseous, ammonia saturated with water vapor (80 psi pressure). Heat the sealed reactor to 95° C. for 45 min. Release the pressure and cool the CPU to room temperature. Elute the oligonucleotide from the CPG with water (~300 µl is sufficient for 50-200 nmol scale synthesis) and proceed to analysis and purification.

All publications, patents and patent applications mentioned in this specification are indicative of the level of skill of those in the art to which the invention pertains. All publications, patents and patent applications are herein incorporated by reference to the same extent as if each individual publication or patent application was specifically and individually indicated to be incorporated by reference in their entirety.

What is claimed is:

1. A process for deblocking substantially a blocked, detectably labeled oligonucleotide comprising contacting the blocked detectably labeled oligonucleotide with an effective amount of a nucleophilic amino compound in the presence of one or more carbohydrates and/or sugars under conditions that result in the deblocking of the oligonucleotide, thereby giving the substantially deblocked oligonucleotide.

2. The process of claim 1, wherein said detectable label is a fluorescent label.

3. The process of claim 1, wherein said nucleophilic amino compound is ammonia.

4. The process of claim 3, wherein said ammonia is present at a psi of about 20 to 200.

5. The process of claim 3, wherein said ammonia is present at a psi of about 80.

6. The process of claim 1, wherein said nucleophilic amino compound is ammonia vapors.

7. The process of claim 1, wherein said nucleophilic amino compound is a $C_{1-6}$ alkylamine.

8. The process of claim 1, further comprising dissolving the substantially deblocked oligonucleotide in a buffer.

9. The process of claim 1, wherein said conditions comprise carrying the process at about room temperature to about 150° C.

10. The process of claim 1, wherein said conditions comprise carrying out the process at about 95° C.

11. The process of claim 1, wherein said conditions comprise carrying out the process for about 1 min to about 2 hrs.

12. The process of claim 1, wherein said substantially blocked, detectably labeled oligonucleotide is immobilized on a solid phase.

13. The process of claim 12, wherein said substantially deblocked oligonucleotide is cleaved from said solid phase under said conditions.

14. A process for deblocking substantially a blocked, detectably labeled oligonucleotide comprising contacting the blocked detectably labeled oligonucleotide with an effective amount of ammonia saturated with water vapor at about 80 psi, 95° C., for about 45 min, thereby giving the substantially deblocked oligonucleotide.

15. The process of claim 14, wherein said blocked, detectably labeled oligonucleotide is immobilized on a solid phase.

16. The process of claim 15, wherein said substantially deblocked oligonucleotide is released cleaved from said solid phase.

17. A composition comprising a blocked, detectably labeled oligonucleotide and an effective amount of a nucleophilic amino compound sufficient to deblock substantially said oligonucleotide and one or more carbohydrates and/or sugars.

18. The composition of claim 17, wherein said detectable label is a fluorescent label.

19. The composition of claim 17, wherein said nucleophilic amino compound is ammonia.

20. The composition of claim 17, wherein said nucleophilic amino compound is ammonia vapors.

* * * * *